(12) United States Patent
Zhang et al.

(10) Patent No.: US 7,778,691 B2
(45) Date of Patent: Aug. 17, 2010

(54) APPARATUS AND METHOD USING SYNCHRONIZED BREATHING TO TREAT TISSUE SUBJECT TO RESPIRATORY MOTION

(75) Inventors: Tiezhi Zhang, Madison, WI (US); Bhudatt R. Paliwal, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1606 days.

(21) Appl. No.: 10/702,810

(22) Filed: Nov. 6, 2003

(65) Prior Publication Data
US 2004/0254773 A1    Dec. 16, 2004

Related U.S. Application Data

(60) Provisional application No. 60/478,584, filed on Jun. 13, 2003.

(51) Int. Cl.
*A61B 5/05* (2006.01)
(52) U.S. Cl. ..................... 600/427; 600/429
(58) Field of Classification Search ............ 600/411, 600/427–429, 407, 413; 378/65, 69
See application file for complete search history.

(56) References Cited

U.S. PATENT DOCUMENTS

| | | | | |
|---|---|---|---|---|
| 3,524,058 A | * | 8/1970 | Wagoner, Jr et al. | 378/95 |
| 3,871,360 A | * | 3/1975 | Van Horn et al. | 600/484 |
| 3,993,995 A | * | 11/1976 | Kaplan et al. | 342/61 |
| 5,317,616 A | * | 5/1994 | Swerdloff et al. | 378/65 |
| 5,538,494 A | | 7/1996 | Matsuda | |
| 5,794,621 A | * | 8/1998 | Hogan et al. | 600/407 |
| 6,076,005 A | * | 6/2000 | Sontag et al. | 600/413 |
| 6,118,847 A | * | 9/2000 | Hernandez-Guerra et al. | 378/65 |
| 6,298,260 B1 | * | 10/2001 | Sontag et al. | 600/413 |
| 6,385,286 B1 | | 5/2002 | Fitchard et al. | |
| 6,501,981 B1 | * | 12/2002 | Schweikard et al. | 600/427 |
| 6,617,852 B1 | * | 9/2003 | Danby et al. | 324/318 |
| 6,889,695 B2 | * | 5/2005 | Pankratov et al. | 128/898 |
| 6,915,005 B1 | * | 7/2005 | Ruchala et al. | 382/131 |
| 7,171,257 B2 | * | 1/2007 | Thomson | 600/427 |
| 2004/0015073 A1 | * | 1/2004 | Schell et al. | 600/411 |
| 2004/0116804 A1 | * | 6/2004 | Mostafavi | 600/428 |

FOREIGN PATENT DOCUMENTS

WO    WO 03/003796 A    1/2003

OTHER PUBLICATIONS

Shinichi, Shimizu, Detection of Lung Tumor Movement in Real-Time Tumor-Tracking Radiotherapy, Int. J. Radiation Oncology Biol. Phys., 2001, 51; 304-310.
S. Jiang, T. Neicu, G.T. Chen, Gated Motion Adaptive Therapy (GMAT): A New Modality for Treating Mobile Tumors, Proceedings of the 44th Annual ASTRO Meeting, Oct. 6-19, 2002.
PCT International Search Report for PCT Application No. USO4/018888, dated Nov. 10, 2004, ISA/EPO.

* cited by examiner

*Primary Examiner*—Long V Le
*Assistant Examiner*—Sanjay Cattungal
(74) *Attorney, Agent, or Firm*—Boyle Fredrickson, S.C.

(57) ABSTRACT

Radiation treatment of the lung or surrounding tissue during continuous breathing is made possible by preparing a treatment plan linked to motion phase and then synchronizing the plan to motion phase as the patient follows a regular breathing schedule.

30 Claims, 7 Drawing Sheets

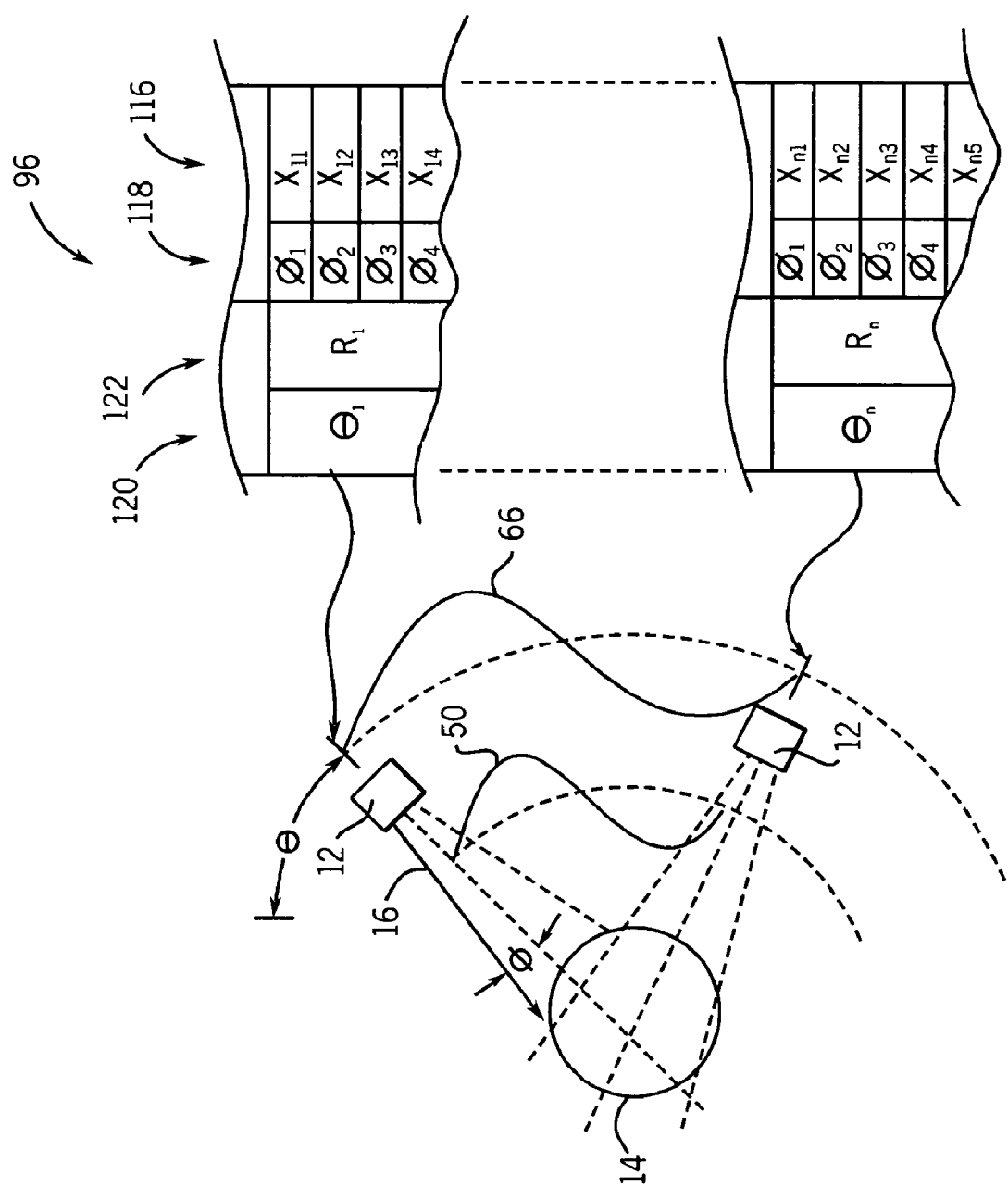

APPARATUS AND METHOD USING SYNCHRONIZED BREATHING TO TREAT TISSUE SUBJECT TO RESPIRATORY MOTION

CROSS-REFERENCE TO RELATED APPLICATIONS

This application claims the benefit of U.S. Provisional application 60/478,584 filed Jun. 13, 2003 which is hereby incorporated by reference.

STATEMENT REGARDING FEDERALLY SPONSORED RESEARCH OR DEVELOPMENT

This invention was made with United States government support awarded by the following agencies: NIH CA88960. The United States has certain rights in this invention.

BACKGROUND OF THE INVENTION

The present invention relates to radiation therapy equipment and in particular to a method and apparatus of using intensity modulated radiation therapy equipment for the treatment of targets subject to respiratory motion such as tumors related to lung cancer and liver cancer.

Intensity modulated radiation therapy (IMRT) systems treat a tumor with converging "beamlets" of radiation (being separately controllable portions of a radiation beam) of different intensities. The overlapping pattern of the beamlets allows the delivered radiation dose to closely conform to complex tumor shapes while minimizing radiation to adjacent tissue.

In first generation IMRT, a two-dimensional multileaf collimator, of a type normally used to outline the radiation beam, is used to control beamlets of a two-dimensional radiation beam according to a speed of movement of each collimator leaf. Radiation is delivered to the patient from a limited number of angles and the patient is stationary. Equipment suitable for conventional IMRT is described in U.S. Pat. No. 4,868,843, hereby incorporated by reference.

In second generation IMRT, such as is taught in U.S. Pat. Nos. 5,317,616; 5,548,627; 5,673,300; 6,438,202; 6,560,311 assigned to the assignee of the present invention and hereby incorporated by reference, a one-dimensional multileaf collimator modulates beamlets of a fan beam by controlling an opening dwell time of each collimator leaf. Radiation is delivered in a plane over 360 degrees and the patient is translated helically or after each rotation to treat a tissue volume.

The pattern and intensity of the different beamlets is determined by a treatment plan typically based on computed tomography (CT) images of the patient on which the tumorous tissue is identified. Computation of beam intensities based on the tumor position and shape uses complex optimization algorithms and is normally done well in advance of the treatment.

The treatment of targets having respiratory motion such as non-small cell lung cancer presents a problem for treatment planning for IMRT equipment because the tumor moves with movement of the lungs over the course of the treatment. Currently, one of three techniques is used to address this problem: gating, breath-hold, and chasing. In the gating technique, patient breathing is tracked and treatment is suspended for phases of the breathing cycle when the tumor is displaced excessively from the location assumed by the treatment plan. Such an approach increases the length of time required for the radiation therapy and, by implicitly allowing some tumor motion during treatment, cannot achieve the highest dose conformity possible with IMRT.

In the breath-hold technique, the patient holds his or her breath on cue or by operation of a valve system. Particularly for patients with lung disease, such breath-hold techniques can be difficult. Because treatment is performed only during breath-holds, the length of time of the treatment over which the treatment is performed is increased.

In chasing techniques, the patient is allowed to breathe regularly following a predetermined pattern and the tumor trajectory is monitored using either a respiratory signal or an implanted marker. The radiation beam is then steered to follow a computed average tumor trajectory by superimposing the tumor movement on motion of movable leaves collimating the radiation beam.

SUMMARY OF THE INVENTION

The present invention provides a general method of using IMRT equipment to treat tissue having periodic motion allowing the patient to breathe continuously, and providing treatment times and dose distributions comparable to those of treating motionless tumors.

In a preferred embodiment, a treatment plan is prepared using a set of CT images at different phases of the breathing cycle. Dynamic lung CT images are generated by 3D image warping using deformation information provided by a biomechanical (solid) model or other image registration methods. Treatment planning incorporating motion is realized by using the beamlets deformed according to the different images. Delivery phases of the treatment plan are linked to phases of the breathing cycle.

Specifically, the present invention provides a treatment planning system for treatment of tumors during periodic organ motion using a radiation therapy machine of a type providing intensity modulated beamlets along a plurality of rays at a plurality of angles about a patient. The planning system provides a model describing the organ at a plurality of phases of organ motion; and a treatment plan calculator which relates treatment phase to phases of organ motion, and determines intensity values for each of the beamlets for each treatment phase using the model of the organ at the phase of organ motion corresponding to the treatment phase.

It is thus one object of the invention to use 3D deformation information of an organ to create a treatment plan for an IMRT machine that accommodates regular periodic motion of the organ during the treatment.

The system may include a model generator having storage holding a solid finite element model of the organ at a first phase of organ motion and at least one image of the organ at a second phase of organ motion; and a deformer warping the solid finite element model according to the image of the organ at the second phase of organ motion.

Thus it is another object of the invention to provide a simple method of generating a model of an organ that reflects changes in the organ with periodic motion.

The treatment plan calculator determines intensity value for each of the beamlets by mapping dose contributions from each beamlet to a single reference image by using curved beamlets on the single reference image, the curve computed to reflect the distortion of tissue of the reference image with different phases of organ motion.

It is thus another object of the invention to provide a simple method of incorporating information about organ motion and warping into conventional treatment planning systems.

In this regard, the present invention also contemplates a radiation therapy system using treatment plans as described above. Such a system provides a radiation source providing intensity modulated radiation along a plurality of beamlets at a plurality of angles about a patient and a respiration monitor providing a respiration signal indicating breathing phase and a controller holding a treatment plan providing intensity values for each of the beamlets for each of the angles linked to a respiration phase, the controller further receiving the respiration signal to vary the intensity of the beamlets according to the treatment plan and the breathing phase.

It is thus another object of the invention to provide a radiation therapy machine that can accommodate continuous breathing by the patient.

The treatment plan may provide intensity values for beamlets distributed over 360 degrees of angle about the patient. Alternatively, the treatment plan may provide intensity values for beamlets distributed multiple angles less than 360 degrees.

It is thus another object of the invention to provide a system that works with first and second generation IMRT systems.

The system may include a patient interface providing an indication to a patient of the respiration signal.

It is another object of the invention to provide a means for allowing a patient to synchronize his or her breathing to a standard pattern.

In this regard, the system may include a generator providing a predetermined respiration schedule; and the patient interface may provide an indication to the patient of the respiratory signal juxtaposed with an indication of the predetermined respiration schedule. The controller may control a phase of the treatment plan according to the predetermined respiration schedule and the patient may match his or her breathing to the predetermined respiration schedule.

It is another object of the invention then to allow continuous breathing by the patient.

The predetermined respiration schedule is a recording of the patient's normal breathing pattern.

It is another object of the invention to allow the patient to adopt a natural and comfortable breathing pattern The patient interface may be glasses having graphic display elements to display a time graph of a respiration signal over time superimposed on a graph of the predetermined respiration schedule.

It is another object of the invention then to provide a simple and intuitive display for the purpose of allowing the patient to match his or her breathing to the standard pattern.

These particular objects and advantages may apply to only some embodiments falling within the claims and thus do not define the scope of the invention.

BRIEF DESCRIPTION OF THE DRAWINGS

FIG. 17 is a diagram of the motion of the radiation source of the system of claim 1 showing synchronization of the patient's breathing with the standard breathing pattern of the treatment plan;

DETAILED DESCRIPTION OF THE PREFERRED EMBODIMENT

System Architecture

Figure 1:
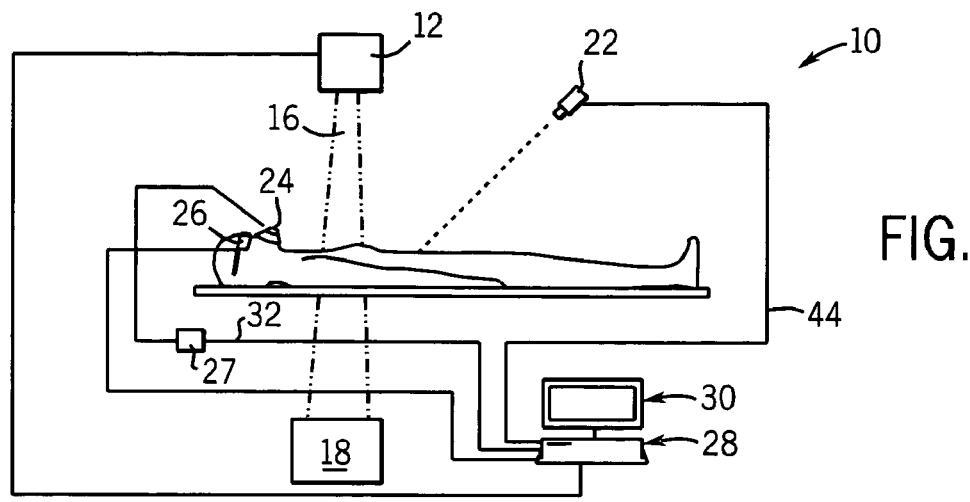
FIG. 1 is a block diagram of a laser-spirometer combined system showing a laser producing a chest displacement signal and spirometer producing a lung volume signal for respiration measurement and a patient positioned to radiation therapy treatment.

Referring now to FIG. 1, an intensity modulated radiation therapy (IMRT) system 10 suitable for use with the present invention provides a radiation source 12. As is understood in the art in a second generation IMRT, the radiation source 12 is a fan beam and may orbit around a patient 14 in a rotational plane parallel to the plane of the fan beam and perpendicular to the plane of the figure transmitting a multi-beamlet radiation beam 16 through the patient 14 to be received by a detector device 18 and/or a radiation stop. The radiation source 12 may be supported for such rotation on a gantry (not shown).

In a first generation IMRT system, the radiation source is a cone beam also positionable about the patient 14, typically to a few selected angles (6-10).

The fan or cone beams are intensity modulated to achieve the best dose distribution according a physician's prescription.

The system shown is also representative of a tomographic imaging system in which case the radiation source 12 is not modulated and the detector device collects projection images to be mathematically combined in a tomographic image according to methods well known in the art.

The patient 14 may be supported in a supine position on a table 20 and the patient's respiration monitored using conventional respiration monitoring such as a chest cuff, displacement sensor, or spirometer.

Alternatively, and as will be described below, the patient's respiration may be monitored with an improved respiration monitor. In this case, the patient is positioned so that a laser displacement sensor 22 (or other displacement sensors) may monitor respiratory motion of the patient's chest. The patient 14 may further breathe through a spirometer 24 measuring airflow into and out of the patient's lungs and the patient may wear video glasses 26 to provide for feedback with respect to the patient's breathing as will be described.

The signal from the spirometer 24 may be preprocessed by an integrator 27 to provide a lung volume signal to a controlling computer 28 which may alternatively receive the signal from the spirometer 24 directly and implement the integrator 27 internally. The computer 28 may also receive a displacement signal from the laser displacement sensor 22 and may communicate with a control terminal 30 such as may include a video screen, keyboard, and mouse or the like. The computer 28 may further control delivery of radiation from the radiation source 12 about the patient 14 and the intensity of the beamlets of the beam 16 by shutters or moving leaves according to methods well known in the art. In the case of an imaging system, the computer may collect the projections and perform a tomographic reconstruction.

Development of an Accurate Respiration Signal

Figure 2:
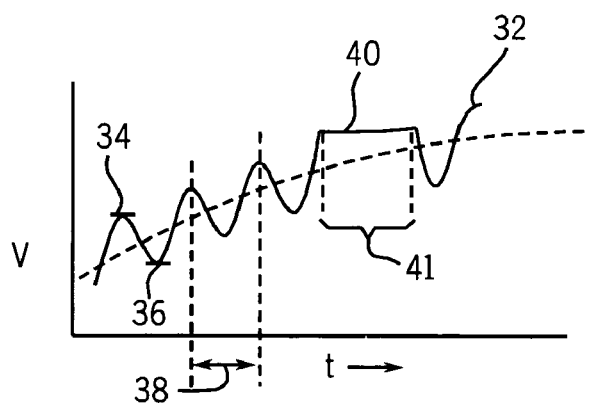
FIG. 2 is a graph of a typical spirometer lung volume signal during both regular breathing and a breath-hold showing drift in the signal.

Referring now to FIG. 2, a typical lung volume signal 32 derived from spirometer 24 shows peaks 34 and troughs 36 corresponding, respectively, to full inspiration and full expiration by the patient 14 during a regular breathing period 38. The present invention contemplates treatment of the patient 14 without the need for breath-holding, however, the respiration signal developed for the present invention may also find use with breath-hold protocols and therefore the lung volume signal 32 during breath-hold is also shown. During the breath-hold, a plateau 40 is created in the lung volume signal 32 reflecting constant lung volume during this breath-hold period 41.

The integration of the output of the spirometer 24 to convert its flow signal (volume/time as a function of time) into a lung volume signal (volume as a function of time) may result in drift, as shown generally by the dotted trend line 42, caused by the integration over time of small offsets in the spirometer signal. Such baseline drift can be confusing to a patient 14 who is attempting to match his or her breathing, as indicated by this drifting signal, to a standard breathing guiding pattern which does not drift.

Figure 3:
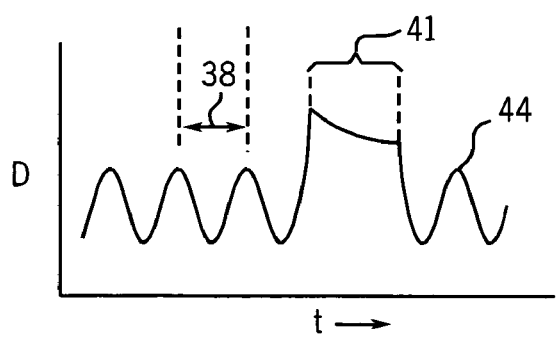
FIG. 3 is a graph of a typical laser chest displacement signal showing a chest contraction at the beginning of a breath-hold.

Referring now to FIG. 3, drift is largely absent from the laser chest displacement signal 44 which does not employ the integrator required of the spirometer 24 but measures chest displacement directly. Generally, the breathing period 38 of the laser chest displacement signal 44 will match the breathing period 38 of the spirometer lung volume signal 32 but the laser chest displacement signal 44 provides a displacement output rather than an output of lung volume. Signal amplitude range variations due to daily setup variations cause deviations between lung volume and chest displacement. Also, during the breath-hold period 41, the laser chest displacement signal 44 decays because of muscle relaxation despite the lack of change in lung volume.

Figure 4:
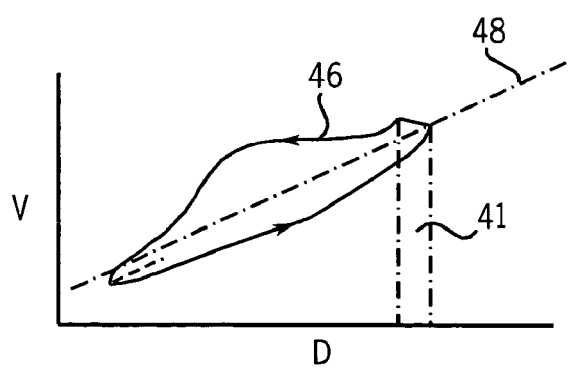
FIG. 4 is a graph of the lung volume signal versus the chest displacement signal showing their correlation and hysteresis.

Referring now to FIG. 4, during a single breathing period 38, there is strong correlation between the lung volume signal 32 obtained from the spirometer 24 and the chest displacement signal 44 from the laser displacement sensor 22 as illustrated by correlation curve 46. The correlation curve 46 plots the lung volume signal 32 on the vertical axis against chest displacement signal 44 on the horizontal axis for one breathing period 38. The points of the correlation curve 46 may be fit to a slope line 48 by a least square fit or other techniques wherein the slope of the slope line 48 provides the correlation between the lung volume signal 32 and the chest displacement signal 44. Generally the correlation curve 46 will have some hysteresis meaning that the functional relationship between lung volume and chest displacement, as displacement increases, is different from the functional relationship between the lung volume and the chest displacement as displacement decreases. The correlation failure between lung volume signal 32 and the chest displacement signal 44 during a breath-hold of breath-hold period 41 is shown by a short flat area in the correlation curve 46.

Because of the drift noted in the lung volume trend line 42 noted above in FIG. 2, correlation curve 46 will generally rise or fall over time preserving approximately the same shape and slope line 48.

Figure 5:
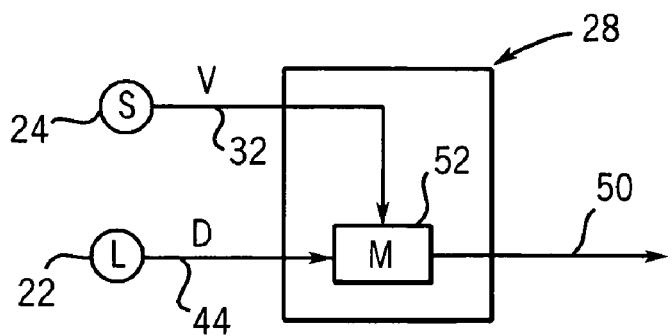
FIG. 5 is a block diagram of the processing of the lung volume signal and chest displacement signal of FIG. 1 to modify the chest displacement signal to produce a corrected respiration signal.

Referring now to FIG. 5, a corrected respiration signal 50 may be obtained by using both the lung volume signal 32 and the chest displacement signal 44 to provide a corrected respiration signal 50 that is both relatively free from drift, calibrated in units of volume, and free from breath-hold artifacts. This correction process may be implemented by model 52 realized preferably as a program running in computer 28.

In a first embodiment, the model 52 receives the lung volume signal 32 and the chest displacement signal 44 to deduce the slope of the slope line 48. The chest displacement signal 44 is then scaled by the slope to translate the chest displacement into units of lung volume, but without drift as the corrected respiration signal 50.

Figure 6:
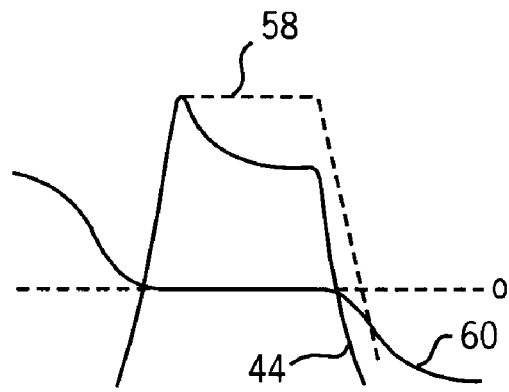
FIG. 6 shows a breath-hold detection system that may be used with the processing of FIG. 5 to further correct the chest displacement signal.

Referring now to FIG. 6, when breath-hold measurements are required, the model 52 may provide for breath-hold-detection to hold corrected respiration signal 50 constant when a breath-hold is detected. In one embodiment, the breath-hold detection may monitor the laser chest displacement signal 44. Breath-hold can be detected from the shape of the chest displacement signal 44 in which the derivative of this signal changes abruptly at the beginning and ending of breath-hold or from spirometer signal 60 in which the flow reading is zero during breath-hold. When a breath-hold is detected, the corrected respiration signal 50 is held to a constant value 58 until the breath-hold is over. Such a system may be used to eliminate the decay artifact of the laser chest displacement signal 44 during the breath-hold period 41.

In a second embodiment, the correlation curve 46 may be captured as a lookup table fitted to a nonlinear equation and used to map arguments of the chest displacement signal 44 to values of lung volume according to the function captured by the correlation curve 46. By detecting an instantaneous change in the input of the chest displacement signal 44 and using the direction of this change to apply the chest displacement signal to either the upper or lower portion of the correlation curve 46, respectively, a model 52 that accommodates hysteresis can be obtained. The use of correlation curve 46 to convert the chest displacement signal 44 into values of lung volume effectively eliminates the decay artifact in the chest displacement signal 44 because the flat portion of the correlation curve 46 during breath-hold period 41 holds lung volume output constant during the breath-hold period 41. The correlation curve 46 may be an average of a number of breathing periods 38 after baseline correction.

Figure 7:
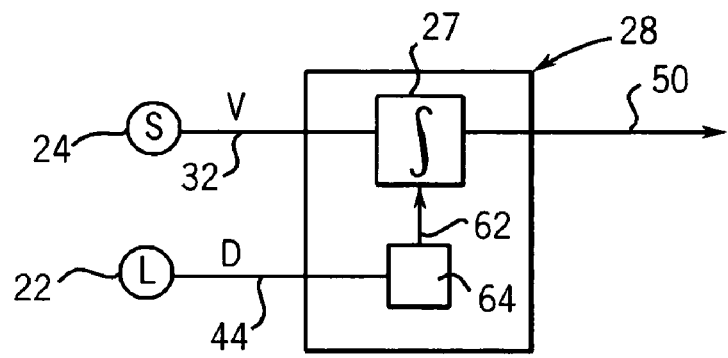
FIG. 7 is a block diagram similar to FIG. 5 of the processing of the lung volume signal and chest displacement signal of FIG. 1 to modify the lung volume signal to produce a corrected respiration signal.

Referring to FIG. 7, the lung volume signal 32 from the spirometer 24 and the chest displacement signal 44 from the laser displacement sensor 22 may also be used to correct the lung volume signal 32 to be the corrected respiration signal 50. In this case, the integrator 27 is preferably implemented within the computer 28 so that the integration constant can be controlled directly. Per this correction process, a correction value is provided by constant generator 64 at a regular period at a given phase in the respiration cycle as determined by the laser displacement sensor (as shown) or the spirometer 24. The correction value is preferably a stored sample of the lung volume signal 32 at the given phase from an early time in the monitoring of respiration when the spirometer signal baseline drift is negligible.

Figure 8:
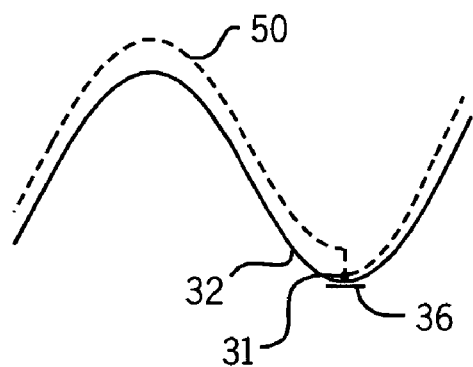
FIG. 8 is a plot of the lung volume signal of FIG. 7 as corrected to produce the corrected respiration signal.

Thus, referring to FIG. 8, at the given phase of the breathing cycle, (for example, full expiration 36) the spirometer lung volume signal 32 is recorded as reference reading 31. The chest displacement signal 44 (not shown) may also be recorded to identify the given phase of the breathing cycle. For later operation, when chest displacement signal 44 reaches the same respiratory phase (amplitude) as the recorded point, the corrected respiration signal 50 is set back to the reference reading 31. In this way, spirometer signal drift is corrected for every cycle and is thereby very small.

Figure 9:
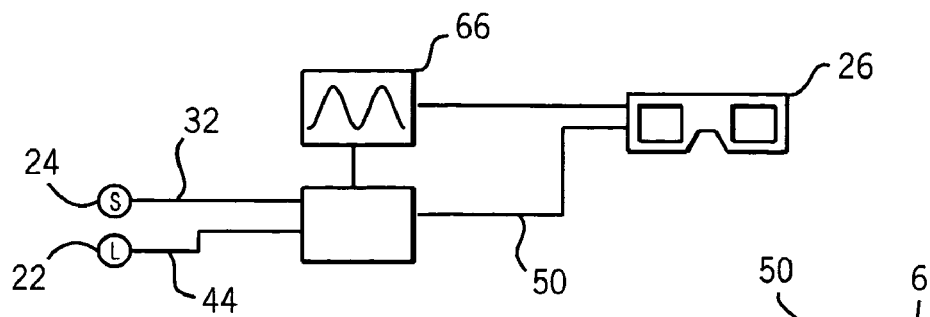
FIG. 9 is a block diagram of a visual feedback system that may be used in the system of FIG. 1 providing a corrected respiration signal and a breathing pattern signal to the patient.

Referring now to FIG. 9, the corrected respiration signal 50 may be displayed to the patient 14 via the glasses 26 together with a pre-established standard breathing guiding pattern 66 preferably obtained from measurements both of the amplitude and periodicity of the patient's ordinary respiration. In this case, the standard breathing guiding pattern 66 may be measured from the patient 14 using the techniques described above and the corrected respiration signals 50 during that measurement stored in computer memory.

Figure 10:
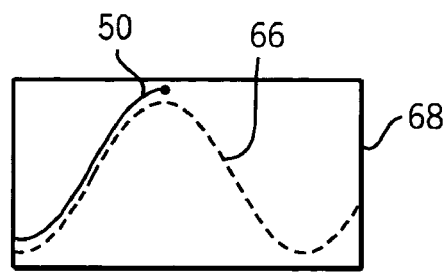
FIG. 10 is a simplified representation of the display of the visual feedback system of FIG. 9.

Referring to FIG. 10, the display 68 of the glasses 26 may show to the patient a full cycle of the standard breathing guiding pattern 66 and a repeatedly drawn corrected respiration signal 50 updated in real time with the horizontal axis scrolling from left to right. The patient 14, observing the corrected respiration signal 50 for his or her current breathing, and the standard breathing guiding pattern 66 may be instructed to conform their breathing to the standard breathing guiding pattern 66. This ability to synchronize the patient's breathing with a stored pattern makes possible the preparation of a treatment plan that is keyed to the standard breathing guiding pattern 66 and which may thus compensate for movement of a tumor in the lung or closely adjacent thereto.

Whereas the present invention does not require breath-hold, the spirometer laser correction system of the present invention may also provide advantages when used in conventional breath-hold situations. Further, it will be understood that the chest displacement signal 44 need not be a laser sensor, but other chest displacement methods including other optical techniques, cuffs, and mechanical transducers may be used.

Use with an Imaging System

Many imaging modalities including x-ray tomography and magnetic resonance imaging create images using a set of measurements acquired over a considerable length of time during which regular physiological motion such as breathing may occur. These measurements which may be x-ray projections or resonance signals acquired with a given set of magnetic gradients are mathematically combined to produce an image. Changes in the position of the tissue during this acquisition process may cause artifacts in the reconstructed images. The present invention may be used to provide a robust respiration signal that may be used to time or order acquisitions according to known techniques to minimize or eliminate these artifacts.

Radiation Therapy with Synchronized Breathing

As will be described in more detail below in the present invention, a treatment plan can be developed for controlling the intensity of the various rays of the radiation source 12 to treat tumor tissue on or near the patient's lungs or other organ having predictable motion. The treatment plan will be provided by the computer 28 which will coordinate operation of the radiation source 12 according to a respiration signal so as to treat the patient 14 during movement of the tumor. During the treatment, the patient 14 may observe a predetermined breathing guiding pattern through the glasses 26 to synchronize his or her breathing to a breathing guiding pattern used in preparation of the treatment plan.

Figure 11:
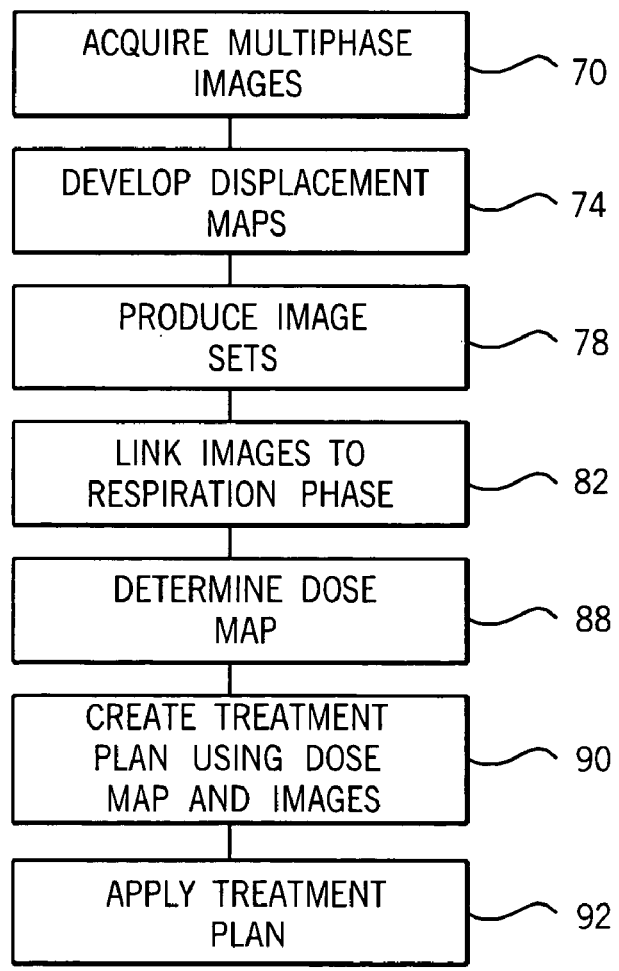
FIG. 11 is a flow chart of the steps employed in the present invention to generate a treatment plan for the system of FIG. 1 that is corrected for lung motion.

Referring now to FIG. 11, in the first step of preparing a treatment plan as indicated by process block 70, CT images are acquired at multiple phases of the patient's normal breathing cycle. This can be achieved by instructing the patient to hold his or her breath at different breathing phases or by using a dynamic CT scan, a commercially available scanning protocol. The dynamic CT scan collects multiple CT images at different phases while a patient breathes normally during scanning.

At process block 74 these multiple CT images are used to develop three dimensional displacement maps at different breathing phases. These displacement maps show displacement of the tissue from a base state (at a given respiration phase, preferably full expiration) and can be obtained by solid modeling or other image registration methods.

Figure 12:
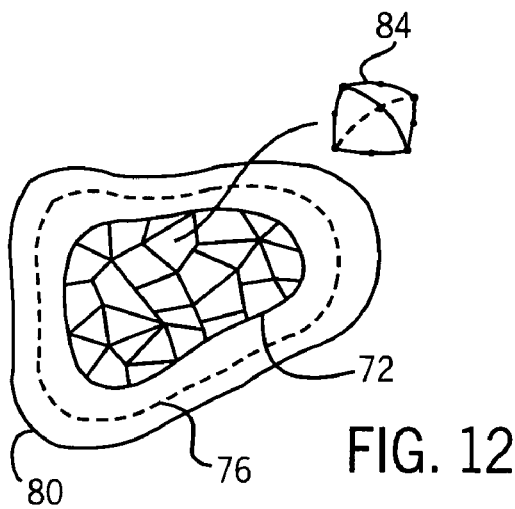
FIG. 12 is a cross-section through a lung of a patient during three stages of the breathing cycle showing generation of a solid model in the lung at a full expiration stage of breathing.

Referring to FIG. 12 in the solid modeling method, a lung surface 72 is extracted from the CT image of the lung at expiration using image segmentation and surface reconstruction techniques well known in the art. This surface is used to generate a solid finite element model. The solid model is filled with tetrahedral elements 84 with nodes along the middle of each side of the tetrahedron.

The surfaces of lung 76 and 80 at other phases are then extracted to form target surfaces whose shape defines the space that the solid lung model can expand.

The model of the lung surface 72 at full expiration may be loaded with a negative surface pressure so that it expands following the normal physics of a solid material composed of a uniform isotropic substance assuming frictionless contact between the lung and the thoracic wall. It is believed that such a modeling is appropriate for normal quiet breathing.

The lung model expands until the space between the lung model and target surface of the lung at the next phase of respiration is closed. A displacement map between the two phases is then obtained by calculating the corresponding nodal position difference before and after deformation. This process is repeated on the lung surfaces at other breathing phases that CT images are acquired. Displacement maps of any other breathing phases can be interpolated from the results of the two closest phases.

Image set 100 having multiple images at different breathing phases are then created, as indicated by block 78, by using the corresponding displacement map and 3D image warping.

At process block 82, each of the images of the image set 100 so created is linked to a respiration cycle angle R with the image of the image set 100 based on the full expiration lung representing a respiration cycle angle of R=0 degrees and the image of the image set 100 based on the full inspiration lung image 80 representing a respiration cycle angle of R=180 degrees. The images of the image set 100 are preferably a registered respiration cycle angle determined from the corrected respiration signal 50 described above but may alternatively be registered to the lung volume signal 32 alone, the chest displacement signal 44 alone, or a breathing signal based on an internal marker position calculated from the internal marker position in the solid model. A time series of images that simulates a patient's breathing is thereby created.

As indicated by process block 88, a dose map 94 (shown in FIG. 13) indicating a desired radiation dose at different positions within the patient with respect to the images for the expiration lung is created using tools and techniques known in the art. With the knowledge of displacement map at the breathing phase, the dose map 94 is mapped into a primary phase, e.g. (expiration phase, R=0).

With the knowledge of delivery-respiration phase correspondence, and the dose map 94, beamlet intensity distributions (a "treatment plan") are calculated by using the images of the image set 100 at the corresponding breathing phase per process block 90.

This treatment plan may then be applied to the patient per process block 92.

Figure 13:
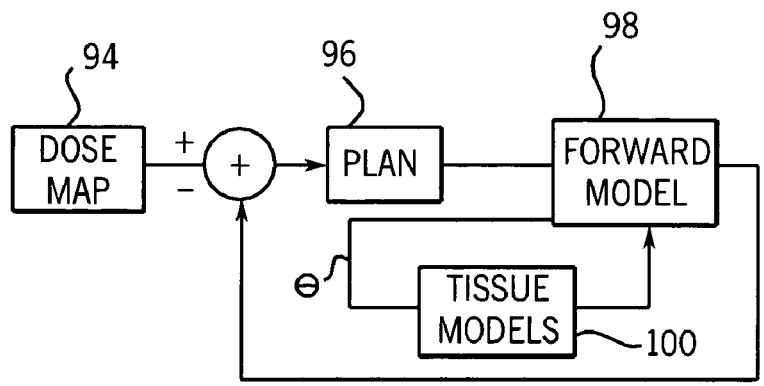
FIG. 13 is a block diagram of the treatment planning system used with intensity modulated radiation therapy and suitable for use with the present invention.

Referring now to FIGS. 1 and 13, these registered images of the image set 100 may be used to generate a treatment plan that accommodates movement of lung and associated tissue per process block 90 through an iterative process. Generally, a treatment plan defines the intensity of multiple rays of the radiation beam 16 for different angles of the radiation source 12 about the patient. The intensities are selected so that the beams at the different angles add with high total intensity on the tumor and add with low intensity on non-tumor tissue.

As described above, a desired tissue dose map 94 is created, for example, as zones superimposed on the image of the expiration lung, each zone mapping desired doses for different elements or node points of the image of the expiration lung. As is understood in the art, the process of determining a treatment plan 96 from a dose map 94 is extremely complex because of the interaction of the multiple rays at different angles. Accordingly, it is common to use an iterative process in which a treatment plan 96 is iteratively adjusted according to one of a number of algorithms, for example, simulated annealing. At each stage of the adjustment, the dose that would result from the treatment plan 96 is modeled per forward model 98. This dose predicted by the forward model 98 is then compared to the desired dose map 94 and the error is used to further adjustment of the treatment plan 96.

The present invention may be integrated into such iterative systems by simply modifying the forward model 98 to reflect anticipated changes in the lung during the treatment process as captured by the image set 100.

For second generation IMRT, this may be accomplished by assuming that there is a fixed relationship between the angle of the radiation beam 16 and the phase of the breathing cycle. Thus, during modeling in the forward model 98 of the dose, the dose is calculated on a different image of the image set 100 depending on the angle of the radiation beam 16 being considered.

Figures 14, 15:
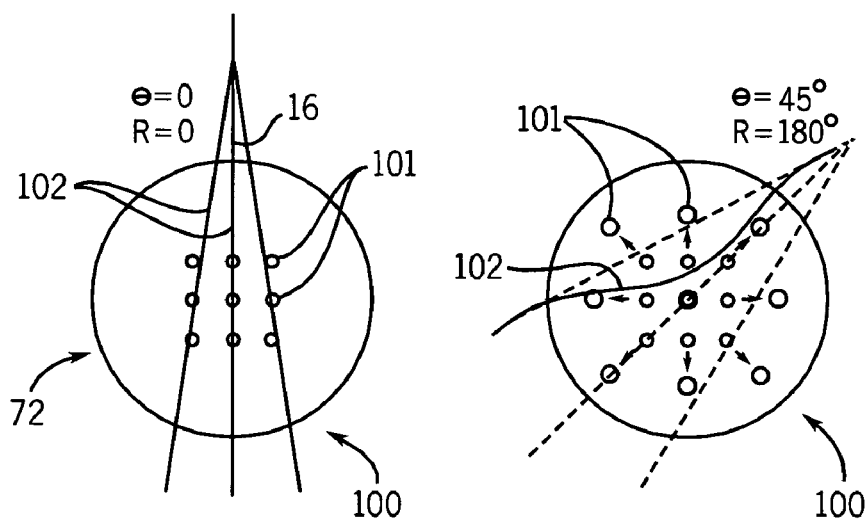
FIGS. 14 and 15 show one method of modification of the dose calculation used in the treatment planning system of FIG. 13 to accommodate lung expansion by modeling curved radiation beams.

Referring now to FIGS. 13, 14, and 15, the forward model 98 may incorporate the expansion of the lung as a function of angle of the beam 16 in a number of ways. In the preferred embodiment, the expansion of the lungs is accommodated by modeling the normally straight beamlets 102 of beam 16 as curved beamlets 102' that follow local tissue dislocations when the lung is expanded.

Thus, as shown in FIG. 14, for a dose map 94 based on the image set of the expiration lung, at a first gantry angle $\theta=0$, and for a respiration cycle angle of R=0, the beamlets 102 of the radiation beam 16 will be modeled in dose map 94 as straight lines through the tissue of image of the expiration lung.

In contrast as shown in FIG. 15, at a later gantry angle $\theta=45$ degrees, at respiration cycle angle of R=180, the lung will conform to the breathing phase associated with full inspiration. In this case, a curved beamlet 102 is used by the dose map 94 based on an expanded image of the image set 100. The curved beamlet 102 allows correct dose placement to be accumulated on the image associated with full expiration by remapping expansion of the tissue to curvature of the beamlet 102. Thus during expansion of the lung, the beamlet 102 curves inward toward the center reflecting the fact that the tissue has in fact expanded relative to the image of the expiration lung used for tallying the total dose.

The treatment plan 96 so generated will differ from a normal treatment plan by describing the intensity of each ray as a function not only of delivery phase but also as a function of respiration cycle angle R. Thus during treatment with the treatment plan 96, the breathing of the patient must be synchronized with the delivery phase $\theta$ and the assumed respiration cycle angle R of the treatment plan 96.

Referring now to FIG. 17, in a second generation IMRT machine, the radiation source 12 produces a radiation beam 16 comprised of a variety of different rays, each identified from an angle from the center of the beam of $\phi$. The treatment plan 96 will include intensity values 116 for each of the rays 118 related to given gantry angles 120 and respiratory cycle angles 122. Generally, the mapping of respiration phase 122 to rotational gantry angle 120 will be selected to accommodate the physical constraints of the radiation therapy system 10 in applying radiation and may include a 1:1 mapping in which one 360 degree rotation of the radiation source 12 corresponds to a single breath cycle (360 degrees) or more typically, multiple breath cycles per each rotation of the gantry.

For a first generation IMRT system, the treatment plan 96 must be derived differently because the relationship between delivery phase and breathing phase cannot be as accurately controlled because of mechanical limitations to leaf movement speeds. For this reason, the optimization process must include an additional level of iteration.

In a first step, shown in block 120, a set of beamlet intensities is developed using the primary image, e.g., at breathing phase R=0, for the several angles of treatment plan anticipated. This treatment plan is prepared per process block 122 using standard planning software for such first generation machines similar to that described with respect to FIG. 13.

The necessary leaf motion sequence to produce the desired beamlet intensities is then calculated by the machine's leaf motion sequence calculator per process block 124 to relate each beamlet intensity to a respiration phase that would exist at the time of the exposure based on movement speed of the shutter and the respiration of the patient following the standard breathing guiding pattern 66 per process block 126. Using these respiration phases, the beamlets are curved per process block 128 and 130, as described above, to reflect the distortion of the tissue caused by respirations. The beamlet intensities are then recalculated using the curved beamlets via optimization process in FIG. 13 again per process block 132. If the difference between the new beamlet intensity and that of previous itineration is within a predetermined tolerance as determined at decision block 134, the planning is complete and a leaf sequence is recorded per process block 136. Otherwise, this process repeats again.

Figure 16:
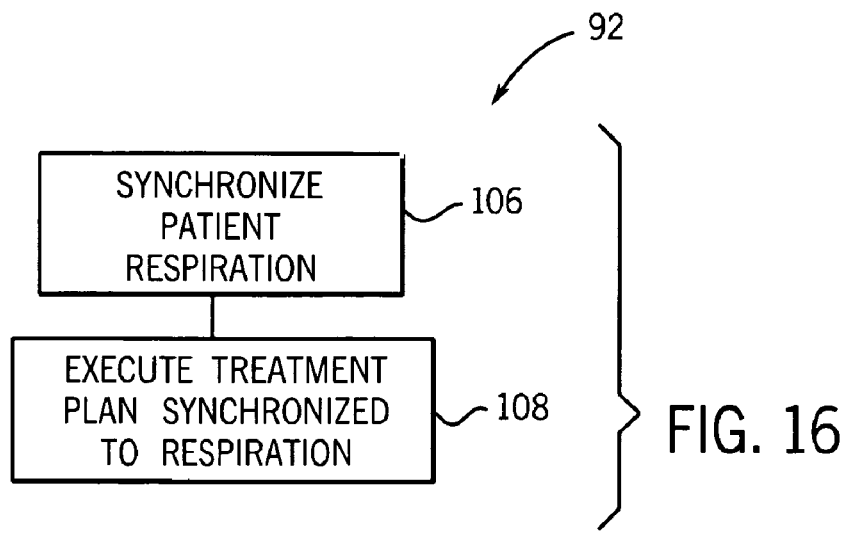
FIG. 16 is a flow chart of the radiation therapy process using the treatment plan generated according to the present invention and breathing control using the corrected respiration signal of the present invention.

Referring now to FIGS. 1 and 16, once the treatment plan 96 has been generated as described, the patient 14 is placed in the radiation therapy machine 10 and the machine pre-positioned at a starting angle (e.g., $\theta=0$). The patient 14 then is instructed to match his or her corrected respiration signal 50 with the standard breathing guiding pattern 66 described above with respect to FIG. 9 by watching the display of FIG. 10 as indicated by process block 106.

Once synchronization has been obtained, such as may be determined automatically by the equipment watching the deviation between corrected respiration signal 50 and breathing guiding pattern 66 of FIG. 3, and when the respiration cycle angle R of the breathing guiding pattern 66 matches at the beginning respiration cycle angle R of the treatment plan 96, treatment delivery 96 is initiated. The treatment continues matching its respiration cycle angle (R) 122 to the respiration cycle angle R of the breathing guiding pattern 66 and matching its delivery phase ($\theta$) to the delivery phase $\theta$ in the plan. In the simplest case, the rate of change of the delivery phase ($\theta$) will be constant and synchronized with the time base of the breathing guiding pattern 66 and the corrected respiration signal 50 will be recorded but does not modify the cycling through the treatment plan 144. However, it will be understood that a simple modification of this embodiment may allow the delivery phase ($\theta$) to speed up or slow down (together with the gantry in a second generation IMRT machine) to attempt to match changes in the respiration cycle angle R of the patient 14 as indicated by corrected respiration signal 50.

It will be understood that in the present invention, the patient may continue to breathe provided that the patient can control the relative phase of his or her breath. This procedure is much more readily tolerated than breath-hold procedures.

Figure 18:
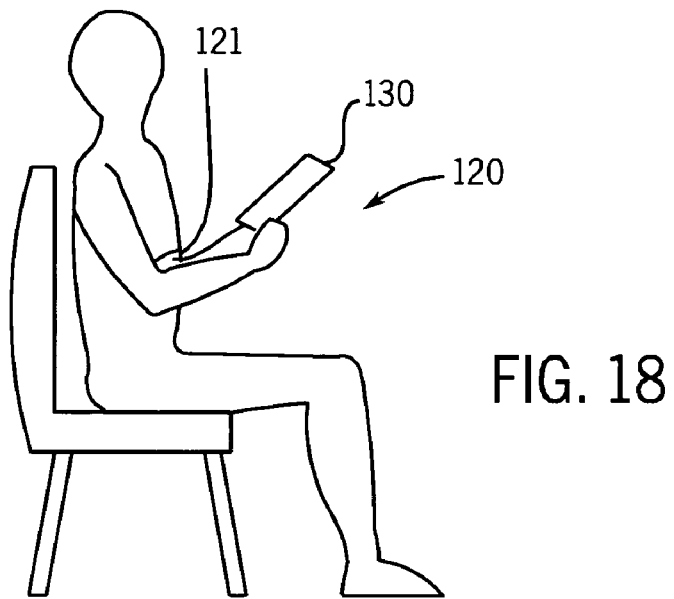
FIG. 18 is a diagram showing a patient using a training system per the present invention.
Figure 19:
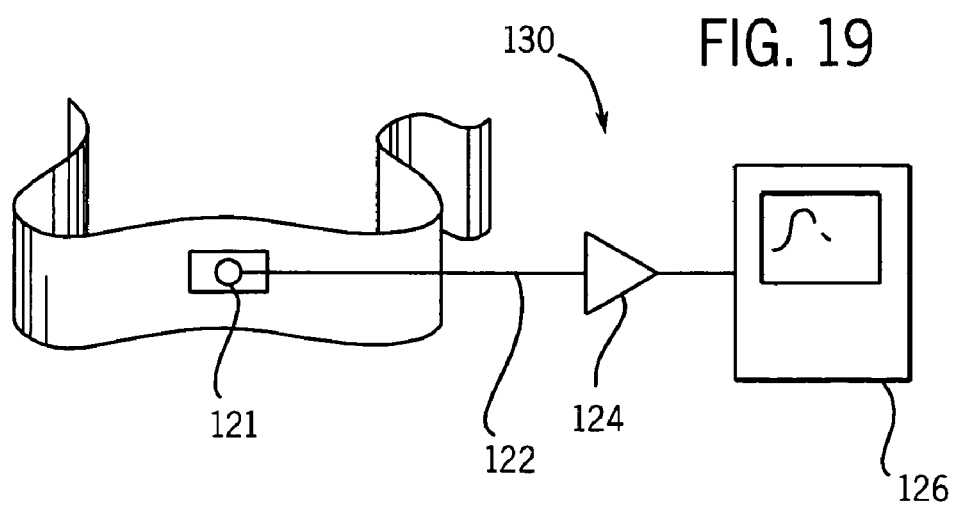
FIG. 19 is a block diagram of the components of the training system of FIG. 18.
Figure 20:
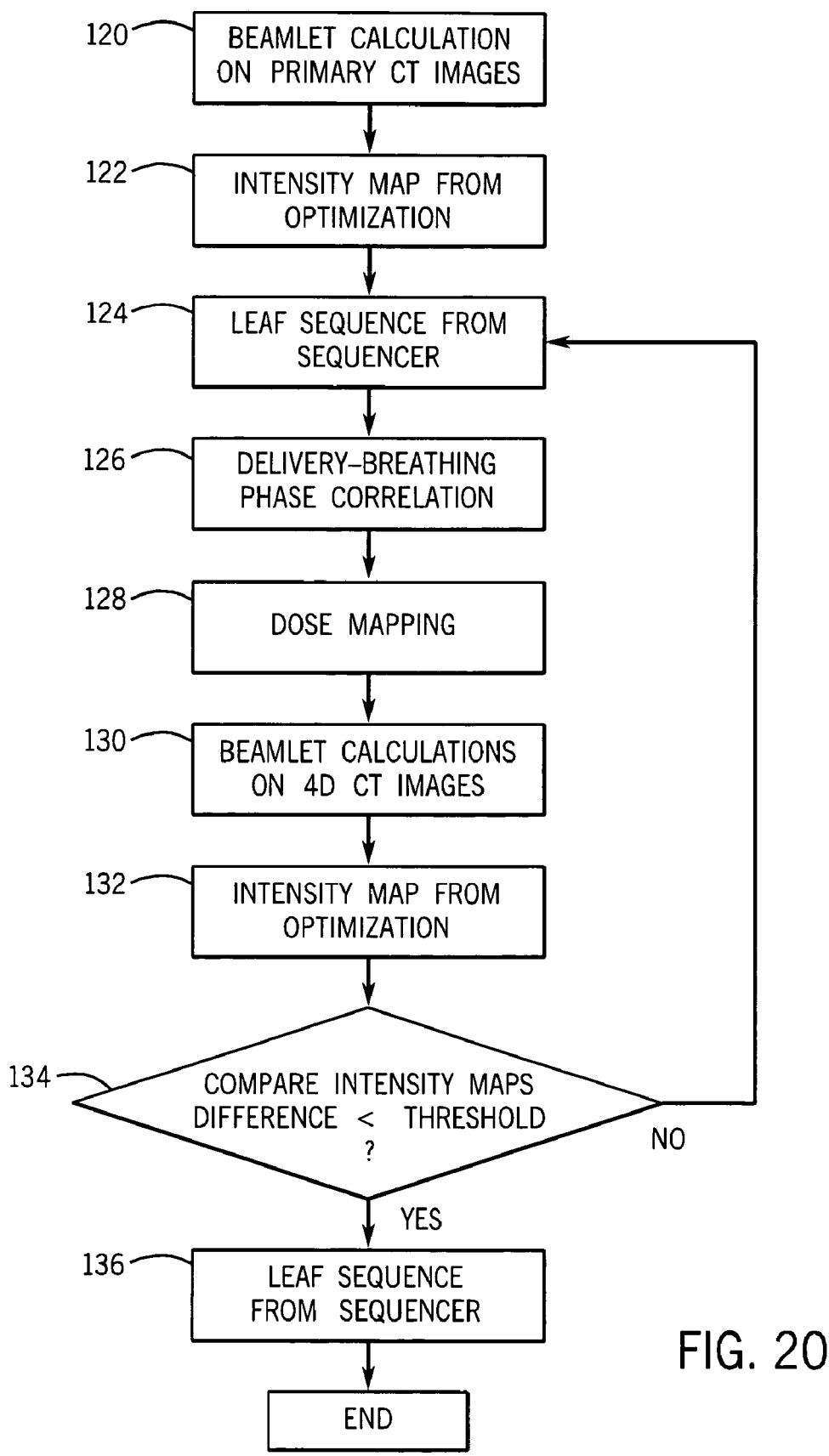
FIG. 20 is a block diagram using this invention on first generation IMRT delivery

In the present invention, the patient may need time to control his or her breathing to track a predetermined breathing schedule during treatment. Referring to FIGS. 18 and 19, a portable patient breathing training system 130 may be used to help patients reduce tracking error. A simple respiratory motion tracking system comprises a pressure sensor 121 or the like detecting abdomen motion. Signals 122 from the pressure sensor 121 are digitized by analog to digital converter 124 and collected on a portable computer such as PDA 126 or the like displaying a stored breathing guiding pattern 66 per FIG. 10 as derived from the patient's normal breathing signal along with a respiration signal derived from the pressure sensor 121.

It is specifically intended that the present invention not be limited to the embodiments and illustrations contained herein, but include modified forms of those embodiments including portions of the embodiments and combinations of elements of different embodiments as come within the scope of the following claims.

We claim:

1. A treatment planning system for treatment of tumors within an organ during periodic organ motion using a radiation therapy machine of a type providing intensity modulated beamlets along a plurality of rays at a plurality of angles about a patient, the planning system comprising:
   a solid finite element model describing positions of tissue elements throughout a volume of an organ at multiple ones of a plurality of phases of organ motion; and
   a treatment plan calculator:
   (i) receiving a dose map corresponding to a first phase of organ motion describing a desired dose of the organ throughout the volume of the organ;
   (ii) relating the dose map to the other phases of organ motion according to the model of the organ;
   (iii) determining from the solid finite element model an intensity value for each of the beamlets using the dose map as distorted for each of the tissue element of the organ at each phase of organ motion; the intensity values taking on a plurality of values ranging between full and zero intensity so that a desired dose is deposited on the tumor and the organ outside the tumor being a summation of the overlapping beamlets along the plurality of rays at the plurality of angles;
   (iv) outputting a treatment plan for the plurality of angles for treatment of a patient wherein the intensity values of the beamlets are a function of the positions of the tissue elements for each of the phases of organ motion, the completed treatment plan formatted for receipt by a radiation therapy machine, the latter using a signal indicating organ motion to read the treatment plan and dynamically change the intensity values of the beamlets per the treatment plan as a function of the signal;
   further including a model generator including:
   (i) a storage means holding an image of the organ at a first phase of organ motion and a displacement map of the organ at a second phase of organ motion; and
   (ii) deforming means warping the organ image using the displacement map.

2. The treatment planning system of claim 1 wherein the model successively warps the images of the organ using displacement maps at multiple phases of organ motion.

3. The treatment planning system of claim 1 wherein the organ is a lung and the phases of organ motion are respiratory phases.

4. The treatment planning system of claim 3 wherein the first phase of organ motion is of the lung in full expiration.

5. The treatment planning system of claim 1 wherein the image is a CT image of the organ.

6. The treatment planning system of claim 1 wherein each phase of treatment is linked to a different delivery phase of radiation.

7. The treatment planning system of claim 1 wherein the treatment plan calculator determines intensity value for each of the beamlets by mapping dose contributions from each beamlet to a single reference image.

8. The treatment planning system of claim 7 wherein the mapping is performed by using curved beamlets on the single reference image, the curve computed to reflect the distortion of tissue of the reference image with different phases of organ motion.

9. The treatment planning system of claim 1 wherein the treatment plan calculator determines intensity values for each of the beamlets for each treatment phase using the model of the organ at the phase of organ motion corresponding to the treatment phase with changes taking into account mechanical limitation to rate of change of beam intensities.

10. The treatment plan calculator of claim 9 where an iterative process is used to determine intensity values from the beamlets incorporating the mechanical limitations.

11. A radiation therapy system for treatment of tumors during respiratory motion comprising:
   a radiation source providing intensity modulated radiation along a plurality of beamlets at a plurality of angles around a patient;
   a respiration monitor providing a respiration signal indicating breathing phase; and
   a controller configured to receive a completed treatment plan for the plurality of angles providing non-zero intensity values between full and zero intensity values for a plurality of the beamlets for the different angles linked to a solid finite element model of tissue elements throughout a volume of the organ at a plurality of respiration phases so that a desired dose is deposited on a tumor and an organ outside the tumor being a summation of the overlapping beamlets along the plurality of rays at the plurality of angles, the controller further configured to receive the respiration signal and synchronizing the plurality of respiration phases in the model with the respiration signal to vary the intensity value of the beamlets according to each respiration phase and variations in the tissue elements with respect to the respiration phases.

12. The radiation therapy system of claim 11 wherein the treatment plan provides intensity values for beamlets distributed over 360 degrees of angle about the patient.

13. The radiation therapy system of claim 11 wherein the treatment plan provides intensity values for beamlets distributed multiple angles less than 360 degrees.

14. The radiation therapy system of claim 11 further including a patient interface providing an indication to a patient of the respiration signal.

15. The radiation therapy system of claim 14 further including:
   a generator providing a predetermined respiration schedule; and
   wherein the patient interface provides an indication to the patient of the respiratory signal juxtaposed with an indication of the predetermined respirations schedule;
   wherein the controller controls a phase of the treatment plan according to the predetermined respiration schedule and the patient may match his or her breathing to the predetermined respiration schedule.

16. The radiation therapy system of claim 15 wherein the predetermined respiration schedule is a recording of the patient's normal breathing pattern.

17. The radiation therapy system of claim 14 further wherein the patient interface is a visual display.

18. The radiation therapy system of claim 17 further wherein the patient interface is goggles having graphic display elements.

19. The radiation therapy system of claim 17 further wherein the display is a time graph of a respiration signal over time superimposed on a graph of the predetermined respiration schedule.

20. The radiation therapy system of claim 15 further including:
   a secondary respiration monitor; and
   a free standing training unit receiving the signal from the secondary respiration monitor and holding the predetermined respiration schedule to provide an indication to the patient of the signal from the secondary respiration monitor juxtaposed with an indication of the predetermined respirations schedule;
   whereby the patient may practice breathing synchronization.

21. A method for treatment of tumors within an organ during periodic organ motion using a radiation therapy machine of a type providing intensity modulated beamlets along a plurality of rays at a plurality of angles about a patient, the treatment comprising the steps of:
   (a) creating a solid finite element model describing the positions of tissue elements throughout a volume of the organ at a plurality of phases of organ motion;
   (b) relating a treatment phase to each phase of organ motion; and
   (c) determining intensity values for each of the beamlets for each treatment phase by distorting a desired dose map for an initial phase of organ motion by the model of the organ at the phase of organ motion corresponding to the treatment phase and changes in the location of the tissue elements throughout the volume of the organ; the intensity values taking on a plurality of intensity values ranging between full and zero intensity so that a desired dose is deposited on the tumor and the organ outside the tumor being a summation of the overlapping beamlets along the plurality of rays at the plurality of angles; and
   (d) outputting a treatment plan for control of the radiation therapy machine synchronizing the treatment phases to motion of the organ, the treatment plan formatted for receipt by the radiation therapy machine so that the radiation therapy machine may use a signal indicating organ motion to read the treatment plan and dynamically change the intensity values of the beamlets per the treatment plan as a function of the signal.

22. The method of claim 21 wherein the step of creating a model acquires an image of the organ at a first phase of organ motion and a displacement map of the organ at a second phase of organ motion; and warps the organ image using displacement map.

23. The method of claim 22 including the steps of acquiring multiple displacement maps and successively warping the images of the organ using displacement maps at multiple phases of organ motion.

24. The method of claim 21 wherein the organ is a lung and the phases of organ motion are respiratory phases.

25. The method of claim 24 wherein the acquired image is of the lung in full expiration.

26. The method of claim 22 wherein the image is a CT image of the organ.

27. The method of claim 21 wherein each phase of treatment is linked to a different delivery angle of radiation.

28. The method of claim 21 including the step of determining an intensity value for each of the beamlets by mapping dose contributions from each beamlet to a single reference image.

29. The method of claim 28 wherein the mapping is performed by using curved beamlets on the single reference image, the curve computed to reflect the distortion of tissue of the reference image with different phases of organ motion.

30. The method of claim 21 including the step of determining intensity values for each of the beamlets for each treatment phase using the model of the organ at the phase of organ motion corresponding to the treatment phase with changes taking into account mechanical limitation to rate of change of beam intensities.

* * * * *

UNITED STATES PATENT AND TRADEMARK OFFICE
CERTIFICATE OF CORRECTION

PATENT NO. : 7,778,691 B2  
APPLICATION NO. : 10/702810  
DATED : August 17, 2010  
INVENTOR(S) : Tiezhi Zhang et al.

Page 1 of 1

It is certified that error appears in the above-identified patent and that said Letters Patent is hereby corrected as shown below:

In the Specification

Column 1, Lines 16-18:
Delete the phrase:
"This invention was made with United States government support awarded by the following agencies: NIH CA88960. The United States has certain rights in this invention."

And replace with:
--This invention was made with government support under CA088960 awarded by the National Institutes of Health. The government has certain rights in the invention.--.

Signed and Sealed this
Eighth Day of December, 2020

Andrei Iancu
*Director of the United States Patent and Trademark Office*